United States Patent [19]

Schoon et al.

[11] Patent Number: 4,785,799
[45] Date of Patent: Nov. 22, 1988

[54] METHOD AND APPARATUS FOR AUTOMATIC PROFILED INFUSION IN CYCLIC TPN

[75] Inventors: JoAnna Schoon, Santa Ana; Robert R. Weyant, Claremont; Gregory B. Zobel, Laguna Niguel, all of Calif.

[73] Assignee: American Hospital Supply Corporation, Evanston, Ill.

[21] Appl. No.: 159,443

[22] Filed: Feb. 18, 1988

Related U.S. Application Data

[63] Continuation of Ser. No. 94,012, Sep. 4, 1987, abandoned, which is a continuation of Ser. No. 763,922, Aug. 8, 1985, abandoned.

[51] Int. Cl.⁴ ............................................. A61M 37/00
[52] U.S. Cl. .................................... 128/53; 604/131; 604/151; 178/DIG. 12
[58] Field of Search ................. 178/DIG. 12; 604/53, 604/65, 93, 131, 151-155, 246, 890.1, 891.1

[56] References Cited

U.S. PATENT DOCUMENTS

| | | |
|---|---|---|
| 3,989,913 | 11/1976 | Lundquist et al. .................. 417/12 |
| 4,270,532 | 6/1981 | Franetzki et al. . |
| 4,282,872 | 8/1981 | Franetzki et al. . |
| 4,308,866 | 1/1982 | Jeliffe et al. . |
| 4,457,750 | 7/1984 | Hill . |
| 4,464,172 | 8/1984 | Lichtenstein . |
| 4,469,481 | 9/1984 | Kobayashi . |
| 4,475,901 | 10/1984 | Kraegen . |
| 4,487,604 | 12/1984 | Iwatschenko et al. . |
| 4,496,351 | 1/1985 | Hillel et al. . |
| 4,498,843 | 2/1985 | Schneider et al. . |
| 4,553,958 | 11/1985 | LeCocg ...................... 128/DIG. 13 |
| 4,624,661 | 11/1986 | Arimond ...................... 128/DIG. 12 |
| 4,692,145 | 9/1987 | Weyant ................................. 604/65 |

Primary Examiner—Edward M. Coven
Assistant Examiner—John C. Hanley
Attorney, Agent, or Firm—Weissenberger & Peterson

[57] ABSTRACT

Cyclic total parenteral nutrition is safely administered by tapering the infusion rate over a substantial period of time at the beginning and end of the infusion cycle. An infusion pump is disclosed which automatically calculates and performs a cycle profile having an appropriate steady-state rate and appropriate tapers in accordance with pre-established criteria when total volume and total infusion time per cycle are entered. The pump has a sleep mode for energy conservation without loss of memory when predetermined periods of inactivity occur.

11 Claims, 3 Drawing Sheets

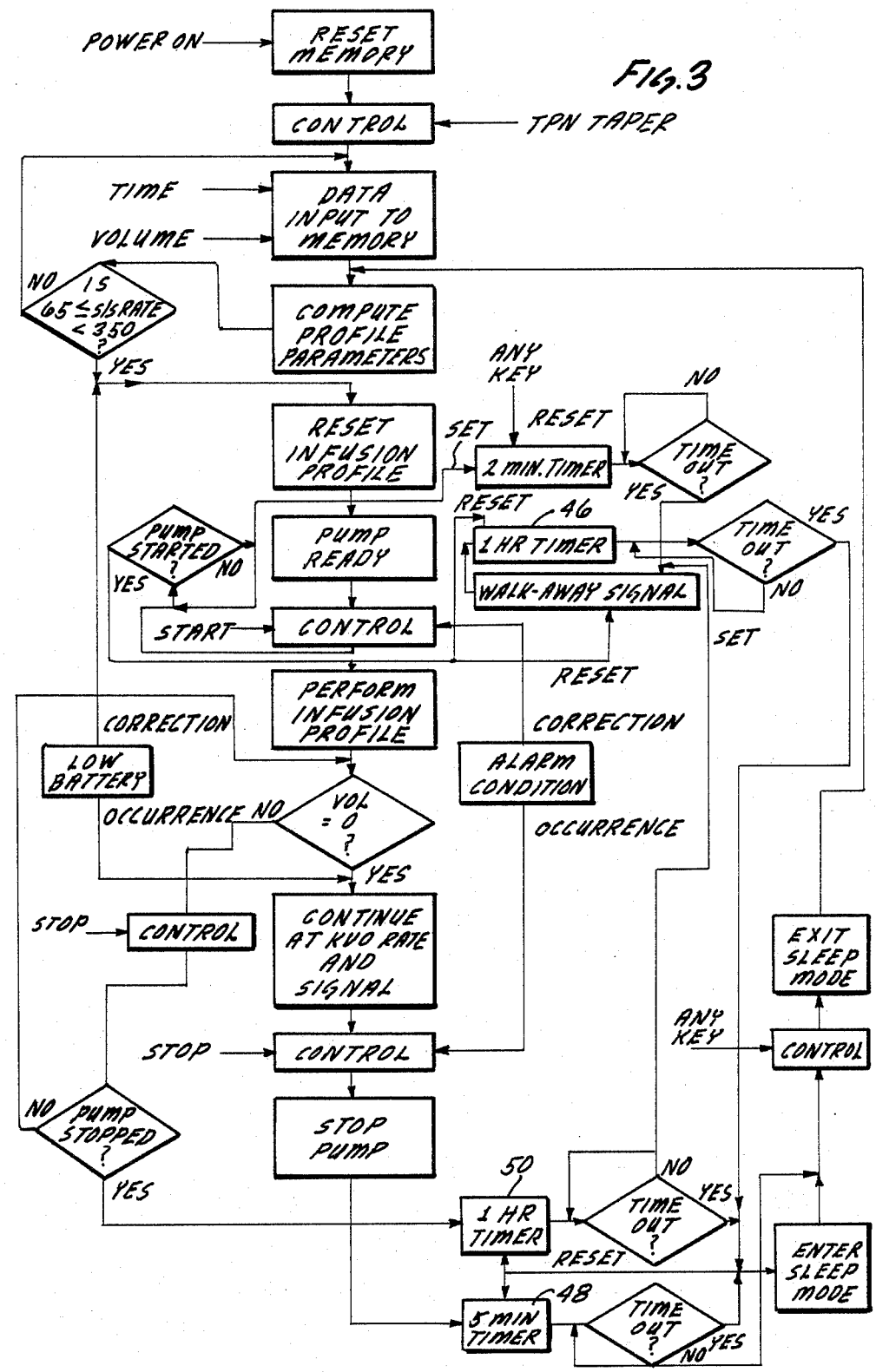

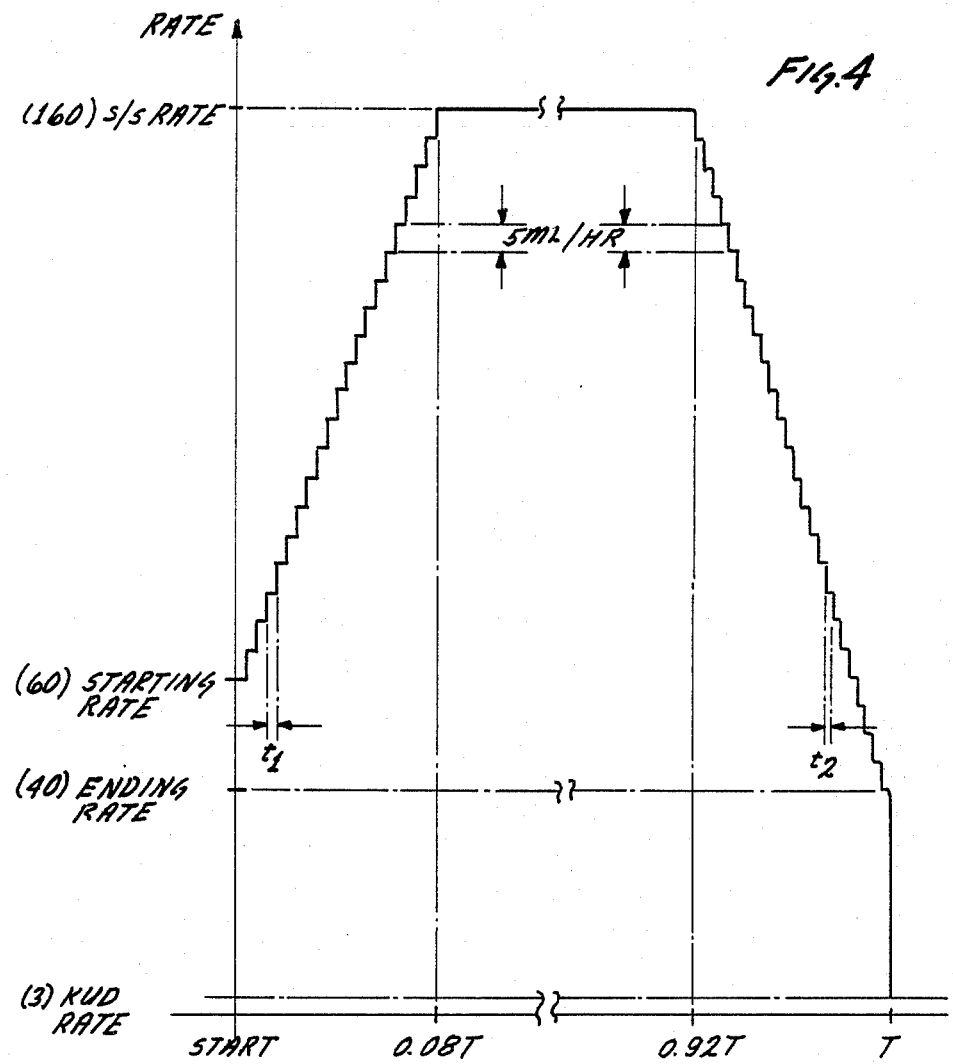
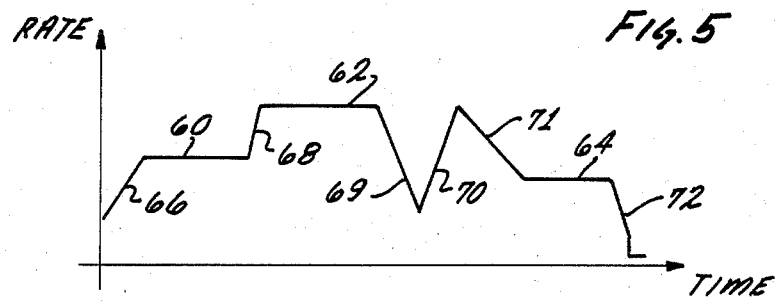

METHOD AND APPARATUS FOR AUTOMATIC PROFILED INFUSION IN CYCLIC TPN

This application is a continuation of application Ser. No. 094,012 filed Sept. 4, 1987, now abandoned, which is a continuation of application Ser. No. 763,922 filed Aug. 8, 1985, now abandoned, and entitled Method and Apparatus for Automatic Profiled Infusion in Cyclic TPN.

This invention relates to cyclic total parenteral nutrition, and more particularly to a method and apparatus for administering the same.

BACKGROUND OF THE INVENTION

Certain diseases in which the body becomes unable to extract nutrition from food in the natural manner require the intravenous administration of large daily quantities of hypertonic dextrose in order to keep the patient alive. Continuous long-term administration of dextrose in this manner makes it necessary to hospitalize the patient for extended periods of time and causes health problems such as fatty infiltration of the liver, hyperinsulinism, lipogenesis, and essential fatty acid deficiency, among others.

Most of the foregoing problems can be prevented or treated by administering total parenteral nutrition (TPN) in a cyclic manner in which the infusion of hypertonic dextrose is discontinued each day for a period of eight to twelve hours. In addition to the direct medical benefits of cyclic TPN administration, considerable psychological benefits are gained by allowing the patient free movement for most of the waking day and making it possible for the TPN to be administered in a home environment.

Cyclic TPN has one disadvantage: sudden starting of TPN at the full steady-state infusion rate is prone to cause clinical symptoms of hyperglycemia and rapid electrolyte influx into the cells because of the inability of the pancreas to suddenly adjust to the high glucose load of the TPN volume. Likewise, sudden cessation of TPN without a tapering-off procedure can cause reactive hypoglycemia.

It has been proposed that patients be instructed to use half the maximum infusion rate for an hour or two at the start of each cycle and to do likewise at the end of each cycle. However, this regimen is only a partial solution to the problem, and is also somewhat impractical in a home environment because the patient may be inattentive or asleep at a time when the infusion rate should be changed.

SUMMARY OF THE INVENTION

To overcome the disadvantages of the prior art described above and to make it possible for a home care patient to self-administer cyclic TPN with a minimum possibility of error, the invention provides an infusion pump which can be programmed to automatically provide clinically appropriate tapering-on and tapering-off of the hypertonic dextrose solution during each cycle of administration.

More specifically, the invention provides for the pump to set and regulate itself in accordance with certain criteria which may either be present within the apparatus or pre-established by the physician. These criteria may typically involve a clinically acceptable starting rate; the proportions of the total cycle time ideally devoted to the taper-on and taper-off procedures, respectively; and a clinically acceptable ending rate. Although one would normally use a single steady-state infusion rate between two tapers, the invention in its broad sense could also be used with appropriate tapers connected by several or no steady-state levels.

With the above-mentioned criteria being preestablished in one form or another, the only daily cycle information or data values which need to be programmed into the pump is the total volume of dextrose to be administered and the total cycle time over which it is to be administered. In accordance with the invention, the pump uses this information to calculate the appropriate tapers and, where applicable, steady-state infusion rate or rates which, in the light of the pre-established criteria, will produce the desired administration cycle.

It is therefore the object of the invention to automatically provide a tapered administration of an infusion in accordance with medically determined criteria.

BRIEF DESCRIPTION OF THE DRAWINGS

FIG. 3 is a general flow chart of the program carrying out the invention.

FIG. 4 is a detailed time-rate diagram illustrating the manner in which an appropriate taper is established.

FIG. 5 is a time-rate diagram showing an example of a multi-steady-state level infusion regimen which could be used with the pump of this invention.

DESCRIPTION OF THE PREFERRED EMBODIMENT

Figure 1:
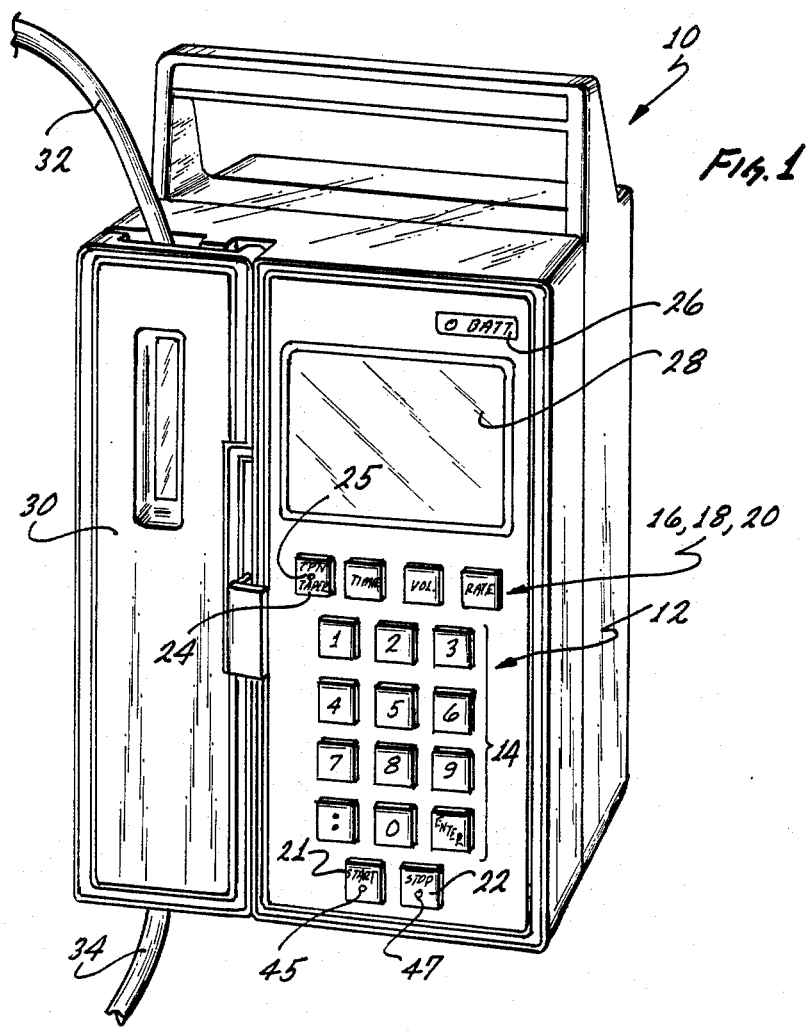
FIG. 1 is an elevational view of an infusion pump adapted to carry out the invention.

FIG. 1 shows an infusion pump adapted for use in connection with this invention. The pump 10 has a conventional keyboard 12 using a set of programming keys 14 as well as time, volume and rate parameter selection keys 16, 18, 20, and start and stop keys 21, 22. In addition, the pump 10 has a special TPN TAPER key 24 with an indicator light 25. The TPN TAPER key 24, when pressed, disables the rate entry and sets the pump 10 into the TPN taper mode of this invention as indicated by illumination of the indicator light 25. Because of the need for the pump to be able to function temporarily in the absence of commercial power, it is provided with a rechargeable battery pack (not shown) whose condition may be indicated by a battery indicator 26. Information relating to the operation of the pump may be shown on a display 28.

A conventional pumping mechanism (not shown) located behind the door 30 pumps fluid from an inlet cannula 32 into an outlet cannula 34 at a rate determined precisely by the internal program of the pump 10.

Figure 2:
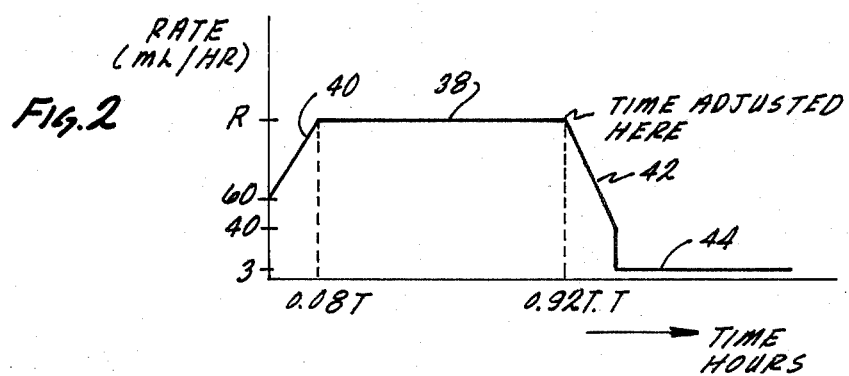
FIG. 2 is a time-rate diagram representative of a preferred tapered administration regimen of the invention.

FIG. 2 shows a preferred tapered time-rate profile of the regimen of this invention. In a typical preferred embodiment, the infusion rate begins at 60 ml/hr and then gradually increases to the steady-state infusion rate R shown at 38. In the preferred embodiment, the interval within which the infusion rate increases from 60 ml/hr to R ml/hr, as shown at 40, is set at 8% of the total administration time T. After that period, the infusion rate remains at R until 92% of the total delivery time T have elapsed. In the final 8% of T, the rate tapers down, as shown at 42, from R ml/hr to a preferred ending rate of 40 ml/hr. When the ending rate has been reached, the pump uses an audible signal that the cycle is complete. It then continues to run at the keep-vein-open (KVO) rate of 3 ml/hr, shown at 44, until it is shut off either manually, or automatically by the exhaustion of the dextrose solution.

The flow chart of FIG. 3 illustrates the operation of the pump 10. When the power to the pump is turned on and the TPM TAPER key 24 is pressed, the pump's memory is clear, and it is ready to accept an input of total cycle time and total volume of solution to be administered per cycle. When these entries have been made, the criteria entered in the criteria registers of the memory, or stored in a permanent read-only memory of the pump, are combined with the time and volume entries to compute the TPN profile parameters in accordance with the formulas set out below.

In the preferred embodiment of the invention in which the infusion rate is tapered up from a predetermined starting rate to a calculated steady-state rate over a predetermined percentage of the total cycle, and tapered down from the steady-state rate to a predetermined ending rate over a predetermined portion of the total cycle time, it will be found that the steady-state rate R in ml/hr is determined by the following formula:

$$R = \frac{2V - T(F_u R_s + F_d R_e)}{T(2 - (F_u + F_d))}$$

in which the keyboard inputs are
V = total volume to be infused (ml)
T = total infusion time (hrs)
and the criteria are
$F_u$ = fraction of T devoted to upward taper
$F_d$ = fraction of T devoted to downward taper
$R_s$ = starting rate (ml/hr)
$R_e$ = ending rate (ml/hr)

In the preferred embodiment using the specific parameters of FIG. 2, it will be seen that the steady-state rate R in ml/hr can be expressed as:

$$R = \frac{1500V - 100t}{23t}$$

where t = total infusion time in minutes.

Once the steady-state rate R has been calculated in accordance with the foregoing formulas, the program checks whether the rate R is within the allowable limits of, e.g., 65 ml/hr and 350 ml/hr, which represent the physiologically acceptable range of steady-state rates for most TPN patients. If the calculated steady-state rate is outside these limits, the program returns to the data input step for selection of another combination of time and volume.

If the steady-state rate is within the allowable limits, and infusion profile such as the profile of FIG. 2 is entered into the pump's memory, and an indicator light 45 on start key 21 is caused to flash to show that the pump 10 is ready for operation. If the pump is not immediately started, a one-hour timer 46 (FIG. 3) is initiated to maintain the pump 10 in the ready mode until it is manually started. During this time an audible walk-away signal may be generated to alert the patient that the pump 10 should be started.

When the start button 21 is pushed, the indicator light 45 changes from flashing to steady, and the pump 10 begins to infuse nutrients in accordance with the calculated infusion profile of FIG. 2, as described in more detail hereafter in connection with FIG. 4. When the cycle has been completed and the volume remaining to be administered is zero, the pump continues to operate at the KVO rate and produces an audible signal to alert the patient that the infusion has been completed.

When the patient thereupon stops the pump by pushing the stop button 22, the indicator light 47 comes on, and the pump remains in an active mode for a short period under the control of a five-minute timer 48 and then enters a sleep mode in which the display 28 is shut off. The pump remains in the sleep mode until the patient pushes any key on the keyboard. At that time, the program retrieves the stored TPN profile information from memory and recalculates the profile parameters in FIG. 2 for another day's cycle.

If the pump 10 is stopped before the remaining volume to be administered is zero, the pump begins to produce the walk-away two minutes after it is stopped, and awaits a restart at the point in the profile where the STOP command occurred. If the pump 10 is not restarted within an hour, the timer 50 causes the pump to go to the sleep mode from which it can only be restarted by performing the profile of FIG. 2 from the beginning. If this presents a clinical problem, the pump 10 can be taken out of the tapered mode by pressing the TPN TAPER key followed by the STOP key 22. The pump 10 may then be operated manually through the keyboard. Patient control over the keyboard may be prevented by entering a keyboard lockout code in a conventional manner after the time and volume settings have been entered.

As is conventional in infusion pumps, several alarm conditions (e.g. air in line, door open, or pump malfunction) may create an alarm condition in which a STOP command is automatically executed by the pump 10. Upon the correction of the alarm condition, the pump restarts at the point in the cycle where it left off, provided the remedial action is taken within the one-hour window set by timer 50.

In the event of a low battery condition (which may interfere with the pump's memory), however, the pump 10 is switched to the KVO rate and is returned to the beginning of the FIG. 2 profile when the low battery condition has been corrected.

FIG. 4 illustrates the operation of the tapers. Inasmuch as continuous adjustment of the pumping rate is impractical due to hardware constraints and the digital nature of the conventional peristaltic pump control mechanism, the transition to or from the steady-state rate R is preferably accomplished in a series of steps which, in the preferred embodiment, are arbitrarily chosen to be increments of 5 ml/hr. As illustrated in FIG. 4, the number of steps depends on the difference between the predetermined starting rate and the calculated steady-state rate. The steepness of the taper is determined by the length of the intervals $t_1$ or $t_2$. The shorter these intervals, the steeper the taper. In the illustrative example of FIG. 4 using the chosen increments, if T is 18 hours and V = 2722 ml, $t_1$ would be 4.32 minutes and $t_2$ would be 3.6 minutes. The step time $t_1$ or $t_2$ can, of course, be calculated by the formulas:

$$t_1 = \frac{5 F_u(60T)}{R - R_s}$$

$$t_1 = \frac{5 F_d(60T)}{R - R_e}$$

It will be understood that the tapered infusion method of this invention is not limited to a single steady-state rate. It is equally applicable to programs which provide for no steady-state rate or for a plurality of steady-state rates 60, 62, 64, interconnected by varying kinds of tapers such as 66, 68, 69, 70, 71, 72 (FIG. 5). Likewise the parameters defining the tapers and the relative steady-state rates may be preset in a read-only memory or may be made changeably presettable at the physician's direction through the keyboard.

What is claimed is:

1. In a programmable medical infusion system including pumping means for pumping an infusion fluid into a patient, means for controlling the pumping means in response to an infusion profile, programmable means for outputting an infusion profile to said means for controlling the pumping means, and input means for inputting data to said programmable means, the improvement comprising:

computing means in said programmable means, responsive to data from said input means of total infusion time and total infusion volume, for calculating, as a function of said time, volume, and predetermined criteria including starting rate, ending rate, and percentage of total infusion time allocated to tapering, an infusion profile having a steady rate preceded by a rate tapering upward from said starting rate to said steady rate, and followed by a rate tapering downward froms aid steady rate to said ending rate, which rates together result in the infusion of said total volume in said total time.

2. The pump of claim 1, further comprising indicating means for indicating the inability of said computing means to calculate said infusion profile when there is no profile capable of satisfying said criteria with said input data values.

3. The pump of claim 1, further comprising signal means for producing a signal if said pump is not manually started within a first predetermined time after said computing means has computed an infusion profile.

4. The pump of claim 1, further comprising display and indicating means for displaying parameters of said infusion profile and indicating the status of said pump, and sleep mode means, actuated when said pump is stopped for a second predetermined time after a profile has been completed, for disabling said display means, indicating means, and computing means but preserving in memory said data values and said criteria.

5. The system of claim 4, further comprising means, responsive to means for re-starting the system after a sleep mode, for causing said computing means to recalculate said profile from said data.

6. The pump of claim 4, further comprising means for causing said sleep mode means to be actuated when said pump is not restarted within a predetermined time after being stopped during an infusion.

7. The pump of claim 1, further including means for controlling said pump to continue pumping said infusion fluid at a keep-veinopen rate following the end of said infusion profile until said pump is shut down manually.

8. The pump of claim 1, in which said tapers are stepped tapers.

9. The pump of claim 1, in which said discrete steps are steps of substantially 5 ml/hr.

10. A method of administering total parenteral nutrition, comprising the steps of:
    (a) selecting a total volume of nutrient fluid to be infused;
    (b) selecting a total time for the infusion of said volume;
    (c) calculating, as a function of predetermined criteria and the total volume and time selected in steps (a) and (b), at least one steady-state infusion rate and at least a pair of infusion rate tapers, which together will result in the infusion of said total volume in said total time; and
    (d) substantially continuously varying the infusion rate in accordance with said tapers before and after the infusion at said steady-state rate; wherein
    (e) said criteria includes a starting rate, an ending rate, and the proportion of said total time allocated to each of said tapers.

11. The method of claim 10, in which each of said pair of tapers spans on the order of 8% of said total time.

* * * * *